(12) United States Patent
Kravitz et al.

(10) Patent No.: US 9,022,978 B2
(45) Date of Patent: May 5, 2015

(54) UNIVERSAL SEALRING CANNULA

(75) Inventors: David Kravitz, Barrington Hills, IL (US); Christopher Steinman, Sandy, UT (US); David Pettinato, Schaumburg, IL (US)

(73) Assignee: Lifeline Scientific, Inc., Itasca, IL (US)

( * ) Notice: Subject to any disclaimer, the term of this patent is extended or adjusted under 35 U.S.C. 154(b) by 393 days.

(21) Appl. No.: 13/097,789

(22) Filed: Apr. 29, 2011

(65) Prior Publication Data
US 2012/0277687 A1 Nov. 1, 2012

(51) Int. Cl.
*A61M 29/00* (2006.01)
*A61M 39/02* (2006.01)
*A61M 1/10* (2006.01)
*A61M 39/28* (2006.01)

(52) U.S. Cl.
CPC .......... *A61M 39/0247* (2013.01); *A61M 39/28* (2013.01); *A61M 39/284* (2013.01); *A61M 1/1008* (2013.01)

(58) Field of Classification Search
USPC ......... 604/244, 164.01, 523, 104–109, 96.01, 604/284.1, 246, 164.11
See application file for complete search history.

(56) References Cited

U.S. PATENT DOCUMENTS

| 3,406,531 A | 10/1968 | Swenson et al. |
| 3,538,915 A | 11/1970 | Frampton et al. |
| 3,545,221 A | 12/1970 | Swenson et al. |
| 3,607,646 A | 9/1971 | de Roissart |
| 3,654,085 A | 4/1972 | Norr et al. |
| 3,660,241 A | 5/1972 | Michielsen |
| 3,777,507 A | 12/1973 | Burton et al. |
| 3,810,367 A | 5/1974 | Peterson |
| 3,843,455 A | 10/1974 | Bier |
| 3,877,843 A | 4/1975 | Fischel |
| 3,881,990 A | 5/1975 | Burton et al. |
| 3,914,954 A | 10/1975 | Doerig |
| 3,935,065 A | 1/1976 | Doerig |
| 3,995,444 A | 12/1976 | Clark et al. |
| 4,006,744 A | 2/1977 | Steer |
| 4,112,944 A * | 9/1978 | Williams ...................... 604/244 |
| 4,186,565 A | 2/1980 | Toledo-Pereyra |
| 4,242,883 A | 1/1981 | Toledo-Pereyra |
| 4,462,215 A | 7/1984 | Kuraoka et al. |

(Continued)

FOREIGN PATENT DOCUMENTS

| DE | 38 08 942 | 9/1989 |
| DE | 43 24 637 A1 | 3/1995 |

(Continued)

OTHER PUBLICATIONS

Sep. 4, 2012 International Search Report issued in Application No. PCT/US2012/033234.

(Continued)

*Primary Examiner* — Bhisma Mehta
*Assistant Examiner* — Phillip Gray
(74) *Attorney, Agent, or Firm* — Oliff PLC

(57) ABSTRACT

Disclosed is a cannula including a first circumferential portion, a second circumferential portion, and a seal with a first clamping surface. The first circumferential portion and the second circumferential portion are configured to mutually cooperate to support a circumference of vasculature, and form a second clamping surface. The first clamping surface and the second clamping surface are configured to cooperate to secure an end of the vasculature.

37 Claims, 4 Drawing Sheets

(56) References Cited

U.S. PATENT DOCUMENTS

| | | | |
|---|---|---|---|
| 4,471,629 | A | 9/1984 | Toledo-Pereyra |
| 4,473,637 | A | 9/1984 | Guibert |
| 4,474,016 | A | 10/1984 | Winchell |
| 4,494,385 | A | 1/1985 | Kuraoka et al. |
| 4,502,295 | A | 3/1985 | Toledo-Pereyra |
| 4,723,974 | A | 2/1988 | Ammerman |
| 4,745,759 | A | 5/1988 | Bauer et al. |
| 4,766,740 | A | 8/1988 | Bradley et al. |
| 4,800,879 | A | 1/1989 | Golyakhovsky et al. |
| 4,837,390 | A | 6/1989 | Reneau |
| 4,951,482 | A | 8/1990 | Gilbert |
| 4,958,506 | A | 9/1990 | Guilhem et al. |
| 5,004,457 | A | 4/1991 | Wyatt |
| 5,141,847 | A | 8/1992 | Sugimachi et al. |
| 5,157,930 | A | 10/1992 | McGhee et al. |
| 5,217,860 | A | 6/1993 | Fahy et al. |
| 5,285,657 | A | 2/1994 | Bacchi et al. |
| 5,326,706 | A | 7/1994 | Yland et al. |
| 5,356,771 | A | 10/1994 | O'Dell |
| 5,362,622 | A | 11/1994 | O'Dell et al. |
| 5,383,854 | A | 1/1995 | Safar et al. |
| 5,385,821 | A | 1/1995 | O'Dell et al. |
| 5,434,045 | A | 7/1995 | Jost |
| 5,472,876 | A | 12/1995 | Fahy |
| 5,496,289 | A | 3/1996 | Wenstrom, Jr. |
| 5,586,438 | A | 12/1996 | Fahy |
| 5,681,740 | A | 10/1997 | Messier et al. |
| 5,723,282 | A | 3/1998 | Fahy et al. |
| 5,728,115 | A | 3/1998 | Westcott et al. |
| 5,814,016 | A | 9/1998 | Valley et al. |
| 5,821,045 | A | 10/1998 | Fahy et al. |
| 5,856,081 | A | 1/1999 | Fahy |
| 5,965,433 | A | 10/1999 | Gardetto et al. |
| 6,046,046 | A | 4/2000 | Hassanein |
| 6,355,010 | B1 | 3/2002 | Barbut |
| 6,626,869 | B1 * | 9/2003 | Bint .................. 604/164.01 |
| 6,726,651 | B1 | 4/2004 | Robinson et al. |
| 7,678,563 | B2 | 3/2010 | Wright et al. |
| 2004/0111104 | A1 | 6/2004 | Schein et al. |
| 2004/0221719 | A1 | 11/2004 | Wright et al. |
| 2006/0247498 | A1 | 11/2006 | Bonadio et al. |
| 2008/0086080 | A1 | 4/2008 | Mastri et al. |
| 2011/0059429 | A1 | 3/2011 | Owen et al. |

FOREIGN PATENT DOCUMENTS

| | | |
|---|---|---|
| EP | 0 096 997 | 12/1983 |
| EP | 0 376 763 A2 | 7/1990 |
| EP | 2 218 407 A1 | 8/2010 |
| JP | 2-258701 | 10/1990 |
| SU | 760972 | 9/1980 |
| WO | WO 91/03934 | 4/1991 |
| WO | WO 91/14364 | 10/1991 |
| WO | WO 93/00808 | 1/1993 |
| WO | WO 96/05727 | 2/1996 |
| WO | WO 96/13288 | 5/1996 |
| WO | WO 96/29865 | 10/1996 |
| WO | WO 96/30111 | 10/1996 |
| WO | WO 97/45527 | 12/1997 |
| WO | WO 99/15011 | 4/1999 |
| WO | WO 00/18226 | 4/2000 |
| WO | WO 02/26034 A | 4/2002 |
| WO | WO 2006/105444 A2 | 10/2006 |
| WO | WO 2008/017329 A1 | 2/2008 |

OTHER PUBLICATIONS

Sep. 4, 2012 Written Opinion issued in Application No. PCT/US2012/033234.

"Organ Preservation", J.H. Southard, Ph.D. and F.O. Belzer, M.D., *Principles of Organ Transplantation* Chapter 10, pp. 194-215, 1989.

"Organko Servierungsmachine OKM 82", Von Dietmer Scholz et al., East German Article, 1983 (with English Translation).

"Preservation of Cerebral Function During Circulatory Arrest and Resuscitation: Hypothermic Protective Considerations", Robert J. White, *Resuscitation*, vol. I, pp. 107-115, 1972.

"Storage and Transport of Heart and Heart-Lung Donor Organs With Inflatable Cushions and Eutectoid Cooling", D.R. Wheeldon et al., *The Journal of Heart Transplantation*, vol. 7, pp. 265-268, 1988.

"MOX®-100 Renal Preservation System", Waters Instruments Medical Group, pp. 2-7, 1982.

"Organ Perfusion Systems: An Evaluation Criteria", Fereydoon Sadri, Ph.D., *T.O.P.S. Medical Corporation*, pp. 1-8, 1987.

Gauke Kootstra et al, "A New Device Towards Intermediate Term Kidney Preservation—An Experimental Study," 1980, pp. 86-89.

Jul. 22, 2013 International Preliminary Report on Patentability issued in International Application No. PCT/US2012/033234.

* cited by examiner

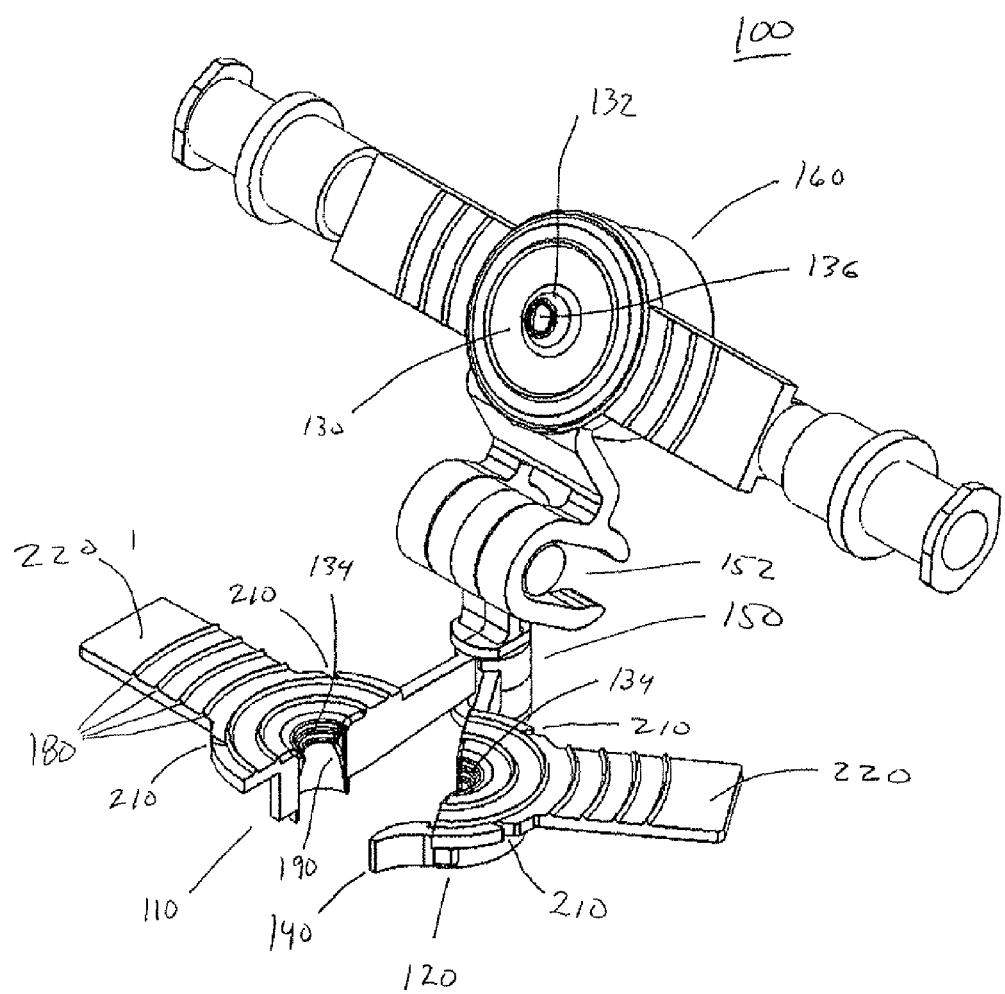

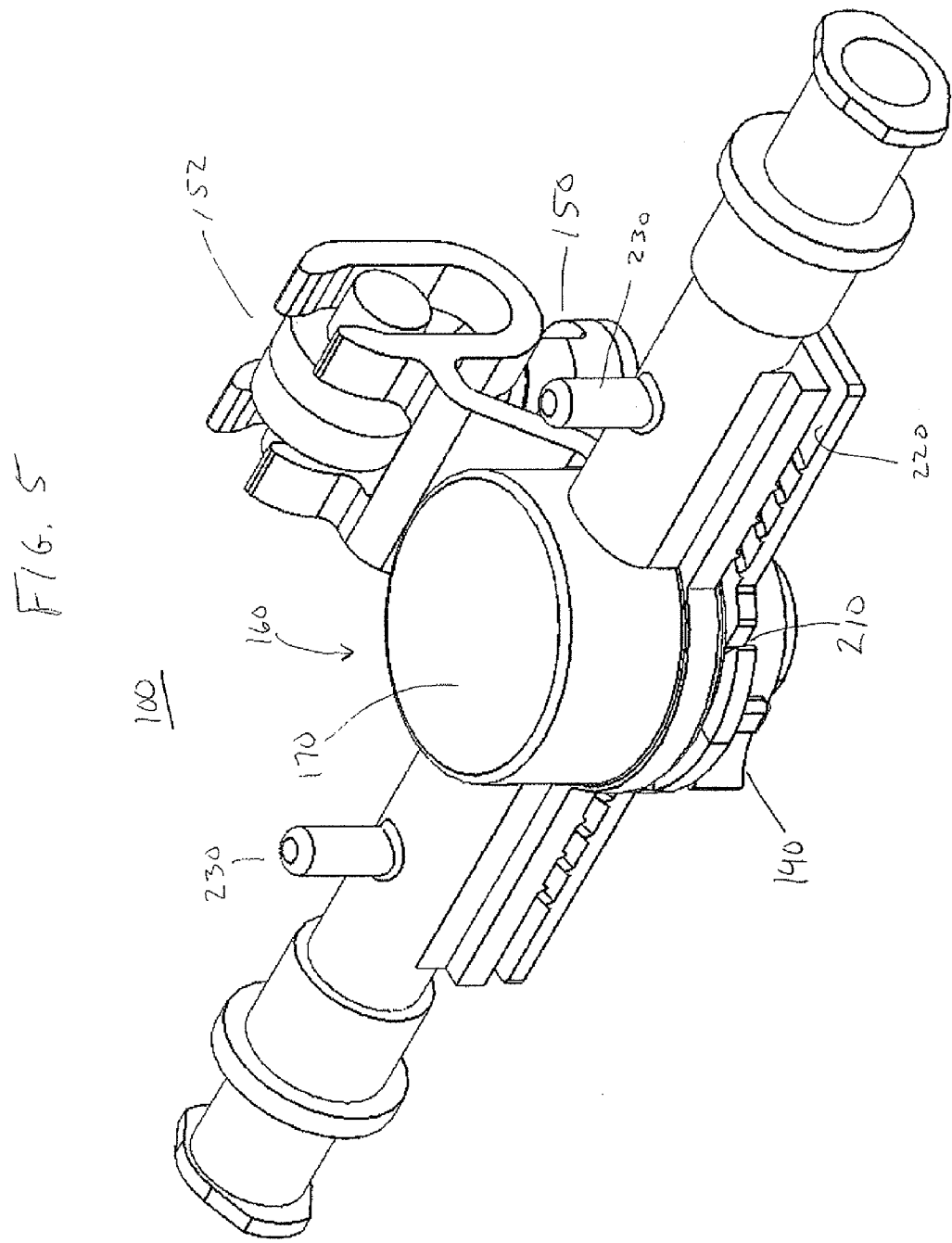

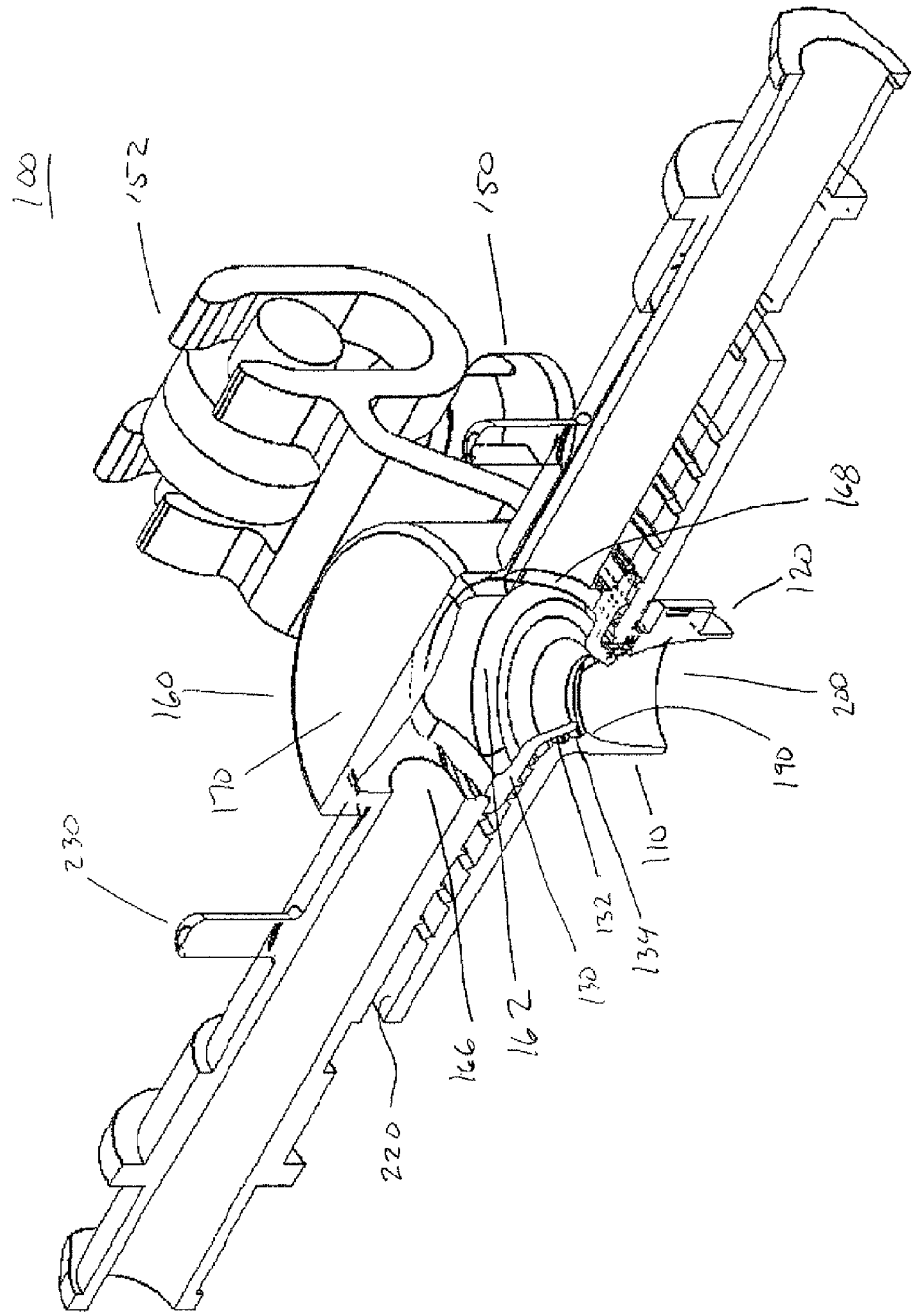

UNIVERSAL SEALRING CANNULA

BACKGROUND

I. Related Technical Fields

Related technical fields include cannulas and clamping methods, and more specifically, cannulas and clamping methods for perfusing one or more organs to monitor, treat, sustain and/or restore the viability of the organ(s) and/or for transporting and/or storing the organ(s).

II. Related Art

Various devices have been developed that couple the anatomy of an organ being perfused to a machine or other equipment. Such devices are typically referred to as perfusion clamps or simply cannulas. Although the term cannula in general use has other meanings, the term cannula is used generically throughout the specification to refer to a clamp or other device that provides a connection through which a fluid flow may be established.

A type of cannula as described in U.S. Pat. No. 5,728,115 to Westcott et al., which is hereby incorporated by reference, is shown in FIGS. 1-3. A clamping device (cannula) 10 is used to couple the perfusion cannula to the renal aorta 34. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an elongated, hollow, annular, integral clamp head 24, while the distal end of the member 14 includes an elongated, hollow, annular, integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in a clamping relationship unless an external compressive force is applied to the handles 18 and 20. A lumen 32 extends through the nipple 28.

In use, the clamp 10 is attached to the renal aorta 34 of a donor organ such as a kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24. A catheter 40 may then be attached to the nipple 28 in order to provide perfusion of liquid through the lumen 32 and into the renal aorta 34

U.S. Patent Application Publication No. 2004/0111104 to Schein et al., which is hereby incorporated by reference, discloses another type of cannula.

SUMMARY

The cannulas as described above require the use of an aortic patch also known as a Carrel patch, or cuff. An aortic patch is a section of the aorta that remains attached to the organ when the organ is removed from an organ donor. The aortic patch is used to facilitate cannulation of vasculature of the donated organ. An aortic patch is typically only available from a deceased donor because of the resultant damage to the aorta required for an aortic patch. As such, the cannulas described above suffer from a problem in that they are not suitable for use with organs, such as a kidney, donated from a living donor or organs where an aortic patch is otherwise not available. With such an organ, the amount of tissue available for cannulation is much less. Care must be taken not to damage the limited amount of tissue available when attaching a cannula so that adequate tissue remains to reconnect the organ when the organ is transplanted to the recipient, and to prevent damage that could result in loss of the organ.

Exemplary implementations of the broad inventive principles described herein provide a cannula that can be used without an aortic patch. Exemplary implementations provide a cannula with a first circumferential portion, a second circumferential portion; and a seal with a first clamping surface. The first circumferential portion and the second circumferential portion are configured to mutually cooperate to support a circumference of vasculature and form a second clamping surface. The first clamping surface and the second clamping surface are configured to cooperate to secure an end of the vasculature. These exemplary implementations provide a solution to problems and disadvantages discussed above because the exemplary implementations do not require an aortic patch and only engage a minimal amount of tissue.

Exemplary implementations of the broad inventive principles described herein provide a method of cannulating vasculature of an organ. The method includes enclosing a circumference of the vasculature with a first circumferential portion of a cannula and a second circumferential portion of the cannula to support the vasculature while maintaining a capability to flow liquid through the vasculature. The method includes contacting an end of the vasculature with a sealing portion of the cannula in a manner that maintains the capability to flow liquid through the vasculature to ensure a substantially leak free condition during perfusion. These exemplary implementations provide a solution to problems and disadvantages discussed above because the exemplary implementations do not require an aortic patch and only engage a minimal amount of tissue.

Exemplary implementations of the broad inventive principles described herein provide a cannula with an optically clear portion configured to allow a user to view at least one portion of an interior of vasculature and a seal when the cannula is in a position in which an end of the vasculature is secured by the cannula. The optically clear portion provides optical magnification of the artery in relation to its position in the cannula. These exemplary implementations provide a solution to problems and disadvantages discussed above because they allow for inspection of the vasculature for damage and proper connection while cannulated. The magnification may also allow the clinician to observe for trapped air bubbles or clots, or to observe the intima of the artery for damage. Also, these exemplary implementations require less tissue from the vasculature to be used because the tissue can be readily viewed in the cannula to confirm that the cannula is properly connected. Thus, excess tissue does not need to be used in order to confirm that the tissue is properly cannulated.

BRIEF DESCRIPTION OF THE DRAWINGS

Exemplary implementations can be described with reference to the following figures wherein:

FIG. 4 illustrates a cannula in an open state;
FIG. 5 illustrates a cannula in a closed state;
and
FIG. 6 illustrates a cross section of a cannula in a closed state.

DETAILED DESCRIPTION OF EMBODIMENTS

Figure 1:
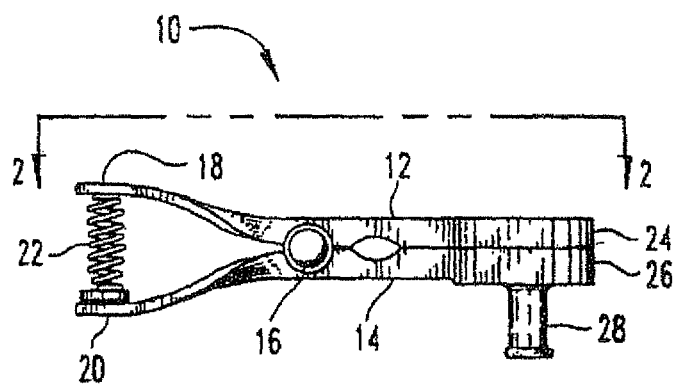
FIGS. 1-3 illustrate a cannula of the prior art.
Figure 2:
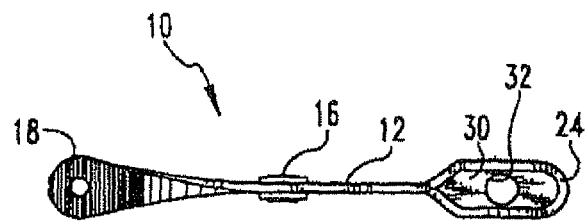
Figure 3:
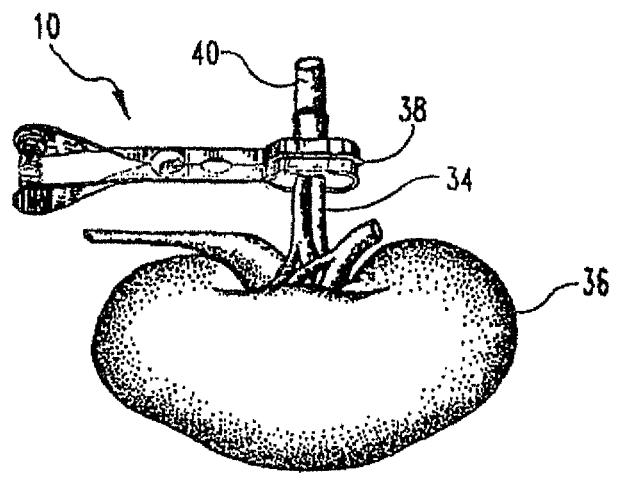

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654 and 5,752,929 and U.S. patent application Ser. No. 08/484,601 to Klatz et al., which are hereby incorporated by reference.

Ideally organs would be procured in a manner that limits their warm ischemia time to essentially zero. Unfortunately, in reality, many organs, especially from non-beating heart donors, are procured after extended warm ischemia time periods (i.e. 45 minutes or more). The machine perfusion of these organs at low temperature has demonstrated significant improvement (Transpl Int 1996 Daemen). Numerous control circuits and pumping configurations have been utilized to achieve this objective and to machine perfuse organs in general. See, for example, U.S. Pat. Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thome et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al., which are hereby incorporated by reference.

The cannulas and clamping methods described herein may be used in conjunction with apparatus and methods described in U.S. Pat. Nos. 6,014,864, 6,183,019, 6,241,945 and 6,485,450 to Owen, which are hereby incorporated by reference. While these apparatus and methods are related to organ recovery and transplantation, the cannulas and clamping methods described herein may also be used in various other medical procedures and with various other medical equipment where clamping with fluid flow is desired. Thus, the cannulas and clamping methods described herein are not limited to the applications described below in conjunction with the exemplary implementations.

FIG. 4 shows a perfusion clamping apparatus or cannula 100 according to a first exemplary implementation. The cannula 100 is capable of connecting one or more arteries of an organ to a perfusion machine or system (not shown), for example, by connection to tubing of the perfusion machine or system. All medical fluid contact surfaces are preferably formed of or coated with materials compatible with the medical fluid used, preferably non-thrombogenic materials.

The medical fluid for perfusion may be any suitable medical fluid. For example, it may be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. Further, the medical fluid may also include blood or blood products.

The cannula 100 is shown in FIG. 4 in an open condition and in FIG. 5 in a closed condition. In the open condition, a first circumferential portion 110 and a second circumferential portion 120 are rotated away from one another on a first hinge 150. The first and second circumferential portions are rotated into contact with one another to form a second clamping surface 134 (described later). When vasculature is disposed between the first circumferential portion 110 and second circumferential portion 120 in such a closed condition, the circumference of the vasculature is supported. A fastening structure 140 secures the first circumferential portion 110 and the second circumferential portion 120 in this closed condition. The fastening structure 140 can be achieved in numerous ways. In the figures, the fastening structure 140 is shown as a releasable snap fit, but other fastening structures, such as a strap or tie will have similar effect. When a releasable snap fit is used, the cannula can be reopened without breaking so that the vasculature can be trimmed or repositioned.

Although the first circumferential portion 110 and the second circumferential portion 120 are shown as rotatably connected at the first hinge 150, other methods of connection are contemplated by the broad inventive principles described herein. For example, at least one of the first circumferential portion 110 and the second circumferential portion 120 could be unattached before closure, and then snap fitted to the other of the first circumferential portion 110 and the second circumferential portion 120. Alternatively, first circumferential portion 110 and the second circumferential portion 120 could translate on pins or rails. Many implementations of relative movement between these two parts are within the broad inventive principles described herein.

Both of the first circumferential portion 110 and the second circumferential portion 120 include a tapered portion 190. As shown in FIG. 6, the tapered portion 190 is narrower in diameter than the cylindrical space 200 formed between the first circumferential portion 110 and the second circumferential portion 120. The tapered portion 190 helps to secure the vasculature, but should not excessively constrict fluid flow through the vasculature. To allow adequate fluid flow within the vasculature, the tapered portion 190 may constrict an outer diameter of the vasculature up to about twelve percent.

After the vasculature is supported between the first circumferential portion 110 and the second circumferential portion 120, a seal 130 is brought into contact with an end of the vasculature. This can be achieved by rotating a chamber portion 160, via a second hinge 152, into a closed position (as shown in FIG. 5), which will bring the seal 130 into contact with an end of the vasculature. In this closed position, the first clamping surface 132 and the second clamping surface 134 secure and end of the vasculature. The complementary conical surfaces of a first clamping surface 132 and the second clamping surface 134 secure the end of the vasculature in a manner that allows free flow of liquid to an interior of the vasculature. Of course, other implementations of movement that secure the end of the vasculature are within the broad inventive principles described herein.

Free flow to and from an interior of the vasculature can be achieved by a flow passage 136. The flow passage 136 may be a circular hole through the seal 130, which may also be circular. The shape of the seal 130 and flow passage 136 are not limited to being circular, and may be influenced by other design considerations.

The seal 130 may be made of an elastomeric material. This will help to prevent damage to the vasculature, particularly an interior of the vasculature, which may be more susceptible to damage than an exterior of the vasculature. The shore A hardness (also known as the durometer) of the seal 130 can be chosen to be within a range of not less than about 32 and not greater than about 70 or within any smaller range therein, such as, preferably not less than about 60 and not greater than about 65. As used herein, the term "about" is intended to account for inherent manufacturing tolerances and inaccuracy in measurement. The hardness may be further tailored within or outside of these ranges depending upon the needs of the vasculature to be cannulated. Seals 130 of various hardness and/or seals 130 with different sizes of the flow passage 136 may be included with the cannula 100 to form a kit that can be used with different vasculatures.

The seal 130 is mated with a first opening (not labeled) in a chamber 162 of the chamber portion 160. The flow passage 136 allows liquid communication from the vasculature to the chamber 162. The chamber portion 160 also includes a second opening 166 and a third opening 168 in fluid communication with the chamber. The second opening 166 and the third opening 168 provide a "lateral" fluid flow, i.e., a flow of fluid that is substantially perpendicular to the direction of fluid flow to and from the tissue to which the cannula is attached. For example, the one or more fittings of the cannula are oriented to have an axis of fluid flow that is substantially perpendicular to an axis of fluid flow into/out of the flow passage 136. This "lateral" fluid flow arrangement allows the cannula to be connected to tubing of an organ transporter, for example, that is substantially in a single plane, for example, as described in U.S. Pat. No. 7,678,563 and U.S. Patent Application Publication No. 2004/0221719, both of which are hereby incorporated by reference. Further, multiple cannulas may be connected and even interconnected within substantially the same plane.

One or both of the second opening 166 and the third opening 168 may be connected to a fitting utilized for priming and/or air bubble removal. A second fitting 107 comprises a port or valve for such purpose. The second opening 166 and the third opening 168 may be may also be used to network multiple cannulas, for example, by connecting tubing in parallel, for example, by running a split infuse line to the first fitting of each cannula, or in series, for example, by connecting the first fitting of a cannula to the second fitting of another cannula. Standard luer geometry or other suitable structure may be used for the fittings.

The chamber portion 160 may include an optically clear portion 170. The optically clear portion 170 allows for visual inspection of the interior of the cannula. This is particularly advantageous in that it allows a user to inspect the clamping of vasculature within the cannula and to inspect for other things such as damage to the vasculature or bubbles within or flowing through the cannula. The optically clear portion may provide optical magnification to allow the user to see more detail of the vasculature, which can be relatively small, perhaps three to seven millimeters in diameter.

As shown in FIG. 4, both the first circumferential portion 110 and the second circumferential portion 120 include a surface 220 that is outside a diameter of the second clamping surface 134 and is approximately perpendicular to a circumference of a vasculature that is supported within the first circumferential portion 110 and the second circumferential portion 120. This surface includes serrations and/or knurls 180. Such serrations and/or knurls 180 may be included to secure additional tissue of the vasculature. Although the cannula 100 is fully operational when securing vasculature without an aortic patch, the surface 220 and serrations and/or knurls 180 cooperate with corresponding structure (not labeled) on the chamber portion 160 to optionally secure an aortic patch. Thus, exemplary implementations of the broad inventive principles described herein provide for a cannula that can be used with or without an aortic patch. For example, when a kidney is cannulated, significant portions of the renal artery may or may not be present. Thus, the cannula 100 can be effectively used in either situation.

The serrations and/or knurls 180 may also be included on the second clamping surface 134. Preferably, there are no serrations and/or knurls on the first clamping surface 132 because the first clamping surface 132 may contact an interior of the vasculature, which is more susceptible to damage. The relatively soft elastomeric material of the seal 130 (and therefore of the second clamping surface 132) will help to prevent damage to the interior surface of the vasculature. The length of the seal that enters the intima of the artery is minimized, therefore minimizing damage to the inside of the artery.

A notch 210 may also be included in one or both of the first circumferential portion 110 and the second circumferential portion 120. Four such notches are shown in FIG. 4. Each notch 210 may be used to secure sutures or side branches of the vasculature. The sutures may be attached to the side branches.

FIG. 5 includes two posts 230. These posts may be used to anchor one or more straps that wrap around the cannula 100 to fasten the chamber portion 160 to the first circumferential portion 110 and the second circumferential portion 120 and keep the cannula in a closed state. Alternative structures may also be used such as a snap fit or ratcheting mechanism.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:
1. A cannula comprising:
a first circumferential portion;
a second circumferential portion; and
a seal with a first clamping surface; wherein
the first circumferential portion and the second circumferential portion are configured to mutually cooperate to:
support a circumference of vasculature, and
form a second clamping surface; and
the first clamping surface and the second clamping surface are configured to cooperate (i) such that, when the cannula is in a closed position, a center axis of the first clamping surface and a center axis of the second clamping surface are coaxial and (ii) to clamp an end of the vasculature between, and in contact with, the first clamping surface and the second clamping surface.

2. The cannula according to claim 1, wherein the first clamping surface and the second clamping surface comprise complementary conical surfaces.

3. The cannula according to claim 1, wherein the first circumferential portion and the second circumferential portion each include at least one fastening structure to cooperatively fasten the first circumferential portion and the second circumferential portion together around the circumference of the vasculature.

4. The cannula according to claim 1, wherein at least one of the first circumferential portion and the second circumferential portion is moveable with respect to the other of the first circumferential portion and the second circumferential portion.

5. The cannula according to claim 4, further comprising a first hinge connecting the first circumferential portion and the second circumferential portion.

6. The cannula according to claim 1, further comprising a flow passage disposed in the seal, the flow passage being configured to allow fluid communication with an interior of the vasculature.

7. The cannula according to claim 1, further comprising a chamber portion having a first opening and a second opening in fluid communication with a chamber, wherein the seal is configured to mate with the first opening.

8. The cannula according to claim 7, wherein the chamber portion comprises a third opening in fluid communication with the chamber.

9. The cannula according to claim 7, wherein the chamber portion is moveable with respect to at least one of the first circumferential portion and the second circumferential portion.

10. The cannula according to claim 7, wherein the chamber portion is connected to at least one of the first circumferential portion and the second circumferential portion by way of a hinge.

11. The cannula according to claim 7, wherein the seal is disposed between the chamber portion, the first circumferential portion, and the second circumferential portion when the cannula is in a position in which the end of the vasculature is secured.

12. The cannula according to claim 1, further comprising an optically clear portion configured to allow a user to view at least one of an interior of the vasculature and the seal when the cannula is in a position in which the end of the vasculature is secured, wherein the optically clear portion provides optical magnification.

13. The cannula according to claim 1, wherein the seal comprises an elastomeric material.

14. The cannula according to claim 13, wherein the elastomeric material has a shore A hardness not less than 32 and not greater than 70.

15. The cannula according to claim 14, wherein the elastomeric material has a shore A hardness not less than 60 and not greater than 65.

16. The cannula according to claim 1, wherein the second clamping surface comprises at least one of serrations and knurls.

17. The cannula according to claim 1, wherein the first circumferential portion and the second circumferential portion each comprise a tapered portion with a smaller diameter than that of a substantially cylindrical space formed between the first circumferential portion and the second circumferential portion.

18. The cannula according to claim 17, wherein the smaller diameter is no more than twelve percent smaller than a diameter of the substantially cylindrical space.

19. The cannula according to claim 1, wherein at least one of the first circumferential portion and the second circumferential portion comprises a notch configured to secure a suture or a side branch of the vasculature.

20. The cannula according to claim 1, wherein at least one of the first circumferential portion and the second circumferential portion comprises a surface located outside a diameter of the second clamping surface, the surface is approximately perpendicular to the circumference, and the surface comprises at least one serration or knurl.

21. The cannula according to claim 7, further comprising a fastening structure configured to secure the chamber portion to at least one of the first circumferential portion and the second circumferential portion when the cannula is in a closed state.

22. The cannula according to claim 21, wherein the fastening structure is an elastomeric strap.

23. The cannula according to claim 21, wherein the fastening structure is a snap fit.

24. The cannula according to claim 21, wherein the fastening structure is a ratcheting mechanism.

25. The cannula according to claim 1, wherein the first clamping surface is movable with respect to the first circumferential portion and the second circumferential portion.

26. The cannula according to claim 1, further comprising:
a chamber configured to be in fluid communication with the vasculature disposed between the first circumferential portion and the second circumferential portion,
wherein, the first circumferential portion and the second circumferential portion form a space therebetween, and
the chamber is coaxial with the space when (i) the first clamping surface and the second clamping surface mutually cooperate to form the second clamping surface and (ii) the chamber is in fluid communication with the vasculature.

27. The cannula according to claim 1, further comprising a hinge connected to the first clamping surface and configured to rotate the first clamping surface toward and away from the formed second clamping surface.

28. The cannula according to claim 1, wherein the first clamping surface and the second clamping surface are configured to cooperate to clamp the end of the vasculature between the first circumferential portion and the first clamping surface and between the second circumferential portion and the first clamping surface, such that the vasculature is in contact with the first clamping surface and the second clamping surface.

29. The cannula according to claim 1, in the form of a kit comprising a plurality of interchangeable seals configured for different sizes of vasculature.

30. A method of cannulating vasculature of an organ, the method comprising:
contacting a circumference of the vasculature with a first circumferential portion of a cannula and a second circumferential portion of the cannula to support the vasculature while maintaining a capability to flow liquid through the vasculature;
contacting an end of the vasculature with a sealing portion of the cannula in a manner that maintains the capability to flow liquid through the vasculature, wherein the vasculature is clamped between, and in contact with, (i) a surface formed by both the first circumferential portion of the cannula and the second circumferential portion of the cannula and (ii) the sealing portion of the cannula such that a center axis of the surface and a center axis of the sealing portion are coaxial.

31. The method according to claim 30, wherein the organ is a kidney and the vasculature does not include an aortic patch.

32. The method according to claim 30, wherein the circumference of the vasculature is compressed no more than twelve percent.

33. The method according to claim 30, further comprising clamping the end of the vasculature between the sealing portion and at least one of the first circumferential portion and the second circumferential portion.

34. The method according to claim 30, further comprising engaging at least one of serrations and knurls with the vasculature no more than two millimeters from the end of the vasculature.

35. A cannula for a vasculature of a kidney without an aortic patch, the cannula comprising:
means for contacting a circumference of the vasculature with a first circumferential portion of the cannula and a second circumferential portion of the cannula to support the vasculature while maintaining a capability to flow liquid through the vasculature;
means for contacting an end of the vasculature with a sealing portion of the cannula in a manner that maintains the capability to flow liquid through the vasculature, wherein the vasculature is clamped between, and in contact with, (i) a surface formed by both the first circumferential portion of a cannula and the second circumferential portion of the cannula and (ii) the sealing portion of the cannula such that a center axis of the surface and a center axis of the sealing portion are coaxial.

36. A cannula comprising:
a first circumferential portion;
a second circumferential portion; and
a seal with a first clamping surface; wherein
    the first circumferential portion and the second circumferential portion are configured to mutually cooperate to:
        support a circumference of vasculature, and
        form a second clamping surface; and
    the first clamping surface and the second clamping surface are configured to cooperate to secure an end of the vasculature between, and in contact with, the first clamping surface and the second clamping surface such that the first clamping surface and the second clamping surface do not damage the vasculature clamped therebetween.

37. A method of cannulating vasculature of an organ, the method comprising:
    contacting a circumference of the vasculature with a first circumferential portion of a cannula and a second circumferential portion of the cannula to support the vasculature while maintaining a capability to flow liquid through the vasculature;
    contacting an end of the vasculature with a sealing portion of the cannula in a manner that maintains the capability to flow liquid through the vasculature, wherein a surface formed by the first circumferential portion of the cannula and the second circumferential portion of the cannula cooperates with the sealing portion to secure the end of the vasculature between, and in contact with, the surface and the sealing portion such that the surface and the sealing portion do not damage the vasculature clamped therebetween.

* * * * *